United States Patent [19]

Chan

[11] Patent Number: 4,912,255

[45] Date of Patent: Mar. 27, 1990

[54] PROCESS FOR PREPARING SODIUM PHENYLPYRUVATE FROM CALCIUM PHENYLPYRUVATE

[76] Inventor: Albert S. Chan, 1233 Danvers Dr., St. Louis, Mo. 63146

[21] Appl. No.: 338,001

[22] Filed: Apr. 13, 1989

[51] Int. Cl.$^4$ .............................................. C07C 59/74
[52] U.S. Cl. .................................................... 562/459
[58] Field of Search ......................................... 562/459

[56] References Cited

U.S. PATENT DOCUMENTS 4,334,089  6/1982  Kraas ................................. 562/459

FOREIGN PATENT DOCUMENTS 132201  1/1985  European Pat. Off. .

Primary Examiner—Paul J. Killos

[57] ABSTRACT

A process for the production of sodium phenylpyruvate from calcium phenylpyruvate wherein calcium phenylpyruvate is contacted with a sodium carbonate salt in an inert atmosphere.

8 Claims, No Drawings

PROCESS FOR PREPARING SODIUM PHENYLPYRUVATE FROM CALCIUM PHENYLPYRUVATE

BACKGROUND OF THE INVENTION

1. Field of the Invention

This invention is a process for converting calcium phenylpyruvate to sodium phenylpyruvate.

L-phenylalanine is a major component in the popular low calorie sweetener aspartame, formally known as L-aspartyl-L-phenylalanine methyl ester. Whereas this is by far the most important and valuable use of this amino acid, it has other minor applications in pharmaceuticals and animal feed supplements. One route to the synthesis of L-phenylalanine involves the production of phenylpyruvic acid as an intermediate. The phenylpyruvic acid is then converted to sodium phenylpyruvate which is then subjected to a transamination reaction with aspartic acid to produce L-phenylalanine.

U.S. Pat. Nos. 4,152,352, 4,351,952 and 4,447,644 disclose a process for the production of an arylpyruvic acid by the carbonylation of aryl alkyl chloride with carbon monoxide, in the presence of an inorganic base and a metal carbonyl compound. A calcium salt of an arylpyruvic acid is produced as an intermediate and is converted to arylpyruvic acid by acidification with HCl and extrattion with ether. Acidification and ether extraction suffer from the following disadvantages. The use of HCl and ether add raw material costs to the process. In addition, because large amounts of ether are required, moving the ether through the reaction system is costly, and the loss of ether represents a pollution hazard.

U.S. Pat. No. 4,518,800 describes a process for preparing crystallized monohydrated sodium phenylpyruvate from benzaldehyde in the presence of ethanolamine and hydantoin.

U.S. Pat. No. 4,621,153 describes a process for obtaining amino acids, e.g. phenylalanine from a fermentation broth. The process involves providing a source of $Ca^{++}$ ions sufficient to precipitate a $Ca^{++}$ amino acid complex, separating the precipitate, dissolving the precipitate at a pH below 8.5 and recovering phenylalanine.

U.S. Pat. No. 4,152,352 also discloses a process for the production of arylpyruvic acids which comprises reacting an arylmethylhalide in a liquid solvent medium with carbon monoxide at pressures of 5–200 bazs in the presence of a catalytic amount of a metal carbonyl compound such as ion, cobalt or nickel and an alkaline earth metal inorganic base.

U.S. Pat. No. 3,215,620 describes a process for removing anionic surfactants from aqueous solutions, using an ion exchange technique.

The present invention provides a process for converting calcium phenylpyruvate to sodium phenylpyruvate in high yield and purity without the eed for organic solvent extraction which is then suitable for subsequent reaction with aspartic acid to produce L-phenylalanine.

SUMMARY OF THE INVENTION

The present invention is directed to a process for producing sodium phenylpyruvate from calcium phenylpyruvate. The process involves contacting calcium phenylpyruvate with a sodium carbonate salt in an inert atmosphere and obtaining a solution of sodium phenylpyruvate.

DETAILED DESCRIPTION

The reaction can be carried out in a closed autoclave reactor or flask of a desired capacity, as a batch process, or in a continuous flow process, e.g. in a vertical column.

In a batch process, the autoclave is charged with a solution of sodium carbonate or sodium bicarbonate in an inert gas atmosphere, and calcium phenylpyruvate is added. Suitable inert gases are those which do not adversely affect the ion exchange reaction of the present invention, e.g. nitrogen or argon or mixtures thereof. The order of charge of the reactants is not critical to the process.

The autoclave temperature oan be at room temperature or slightly below and thereafter increased to a temperature wherein ion-exchange takes place between the calcium and sodium ions. The process can be carried out at a temperature range of from about 20° to 150° C. At a lower temperature within this range, the reaction proceeds at a slower rate. A preferred temperature range is from about 60° to 100° C.

The reaction mixture is stirred and the autoclave allowed to cool to ambient temperature, about 25° C. The solution of sodium phenylpyruvate obtained is separated from impurities present by conventional liquid separation techniques, for example, decanting or filtering. As referred to earlier, the solution can be used in a transamination reaction with aspartic acid, or a precipitate of sodium phenylpyruvate can be obtained by evaporation of the water.

Alternatively, a continuous flow process for the production of sodium phenylpyruvate can be carried out under an inert gas atmosphere in a vertical column.

The following Examples are provided to better illustrate and define the present invention. They are presented for illustrative purposes only and since minor variations in the methodologies or materials will become apparent to those skilled in the art, they are not to be construed as limiting the spirit and scope of the claims.

EXAMPLE I

Crude calcium phenylpyruvate starting material was produced by the carbonylation of benzyl chloride with CO, in the presence of an inorganic base and a metal carbonyl catalyst. The crude calcium phenylpyruvate was analyzed by a HCl/ether extraction procedure and determined to contain calcium phenylpyruvate which is equivalent to 31.9 wt.% phenylpyruvic acid in the crude material.

16 gm of $Na_2CO_3$ was dissolved in 80 gm $H_2O$ at about 25° C., placed in a 2-liter flask and sparged with nitrogen. An 8 gm portion of crude calcium phenylpyruvate was added to the $Na_2CO_3$ solution, the mixture was heated to 60° C. and stirred for 40 minutes under a nitrogen atmosphere.

The mixture was then cooled to about 25° C. and filtered. The clear filtrate obtained was analyzed by HPLC with a Zorbax C8 column.

A yield of 3.2 gm sodium phenylpyruvate monohydrate was obtained, which was calculated to be a 100 percent yield based on the starting weight of calcium phenylpyruvate.

EXAMPLE II

For comparative purposes, the production of sodium phenylpyruvate by the above-described procedure was carried out, except that the reaction was carried out in air, instead of under an inert atmosphere.

16 gm of $Na_2CO_3$ was dissolved in 80 gm $H_2O$ at a temperature of 25° C. and placed in a 2-liter flask with an air atmosphere. An 8 gm portion of crude calcium phenylpyruvate, produced as described in Example I, was added to the $Na_2CO_3$ solution and the mixture was heated to 60° C. and stirred in air for 40 minutes.

The mixture was then cooled to about 25° C. and filtered. The clear filtrate was analyzed as described in Example I. A yield of 2.45 gm of sodium phenylpyruvate monohydrate was obtained, which was calculated to be a yield of 77 percent, based on the starting weight of calcium phenylpyruvate. This result indicated that carrying out the reaction in an air atmosphere instead of in an inert atmosphere caused a drastic decrease in the yield of sodium phenylpyruvate obtained.

EXAMPLE III 2 gm of commercially-available phenylpyruvic acid (obtained from Sigma Chemical, St. Louis, Mo.) was stirred with 1 gm of $Ca(OH)_2$ in 34.7 ml of $O_2$-free $H_2O$ (which had been sparged with nitrogen for 20 minutes) to produce a suspension of calcium phenylpyruvate. In a similar manner, 1.6 gm of $Na_2CO_3$ was dissolved in 24.5 gm $O_2$-free water and the $Na_2CO_3$ solution added to the calcium phenylpyruvate suspension. The mixture was placed in a 500 ml flask at a temperature of about 25° C. and heated to 60° C., and stirred for 40 minutes under a nitrogen atmosphere.

The mixture was then cooled to about 25° C. and filtered. The clear filtrate was analyzed as described in Example I. A yield of 2.5 gm of sodium phenylpyruvate monohydrate was obtained, which was calculated to be a 100 percent yield based on the starting weight of calcium phenylpyruvate.

EXAMPLE IV 2 gm of commercially-available phenylpyruvic acid was stirred in a 500 ml flask with 1 gm $Ca(OH)_2$ in 35 ml of $H_2O$ in an air atmosphere at about 25° C., to produce a suspension of calcium phenylpyruvate. 1.6 gm of $Na_2CO_3$ was dissolved in 25 ml of $H_2O$ at about 25° C. and the $Na_2CO_3$ solution added to the calcium phenylpyruvate, heated to 60° C. and stIrred in air for 40 minutes.

The mixture was then cooled to about 25° C. and filtered. A yield of 1.96 gm sodium phenylpyruvate monohydrate was obtained, Which was calculated to be a yield of only 79 percent, based on the starting weight of calcium phenylpyruvate.

EXAMPLE V 16 gm of commercially-available phenylpyruvic acid was stirred with 10 gm of $Ca(OH)_2$ in 200 ml of $O_2$-free $H_2O$ (which had been sparged with nitrogen for 20 minutes), to produce a suspension of calcium phenylpyruvate.

13 gm of $NaHCO_3$ was added to the calcium phenylpyruvate and the reaction temperature qradually increased to 100° C. over a 20-minute period, and stirred for 10 minutes at 100° C.

The mixture was then cooled to about 70° C., and the stirring continued for about 30 minutes. The solution obtained was filtered under a nitrogen atmosphere. The material present in the filter was washed twice with degassed $H_2O$ and the washings combined with the filtrate. A yield of 19.84 gm sodium phenylpyruvate monohydrate was obtained, which was calculated to be a 99.7 percent yield based on the starting weight of calcium phenylpyruvate

What we claim is:

1. A process for preparing sodium phenylpyruvate from calcium phenylpyruvate which comprises contacting calcium phenylpyruvate with a sodium salt of a carbonate, under an inert atmosphere, and obtaining therefrom an aqueous solution containing sodium phenylpyruvate.

2. A process as claimed in claim 1, wherein the sodium salt is selected from the group comprising sodium carbonate or sodium bicarbonate.

3. A process as claimed in claim 1, wherein the inert atmosphere is selected from the group comprising nitrogen, argon or a mixture thereof.

4. A process as claimed in claim 1, wherein the reaction is carried out at a temperature of from about 20° to 150° C.

5. A process for preparing sodium phenylpyruvate from calcium phenylpyruvate which comprises contacting calcium phenylpyruvate with sodium carbonate under a nitrogen atmosphere and obtaining therefrom an aqueous solution containing sodium phenylpyruvate.

6. A process as claimed in claim 5 wherein the reaction is carried out at a temperature of from about 20° to 150° C.

7. A process as claimed in claim 6 wherein the reaction temperature is from about 60° to 100° C.

8. A process as claimed in claim 5 wherein the aqueous solution is evaporated and a precipitate of sodium phenylpyruvate is obtained.

* * * * *